United States Patent [19]

Christopher

[11] Patent Number: 5,101,820
[45] Date of Patent: Apr. 7, 1992

[54] APPARATUS FOR HIGH CONTINUOUS FLOW AUGMENTATION OF VENTILATION AND METHOD THEREFOR

[76] Inventor: Kent L. Christopher, 9086 E. Colorado Cir., Denver, Colo. 80231

[21] Appl. No.: 431,026

[22] Filed: Nov. 2, 1989

[51] Int. Cl.$^5$ ............................................. A61M 16/00
[52] U.S. Cl. .......................... 128/204.18; 128/203.25; 128/203.26; 128/207.14
[58] Field of Search .............. 128/201.21, 203.25, 128/203.26, 204.17, 204.21, 204.23, 205.11, 207.14, 207.15, 207.16

[56] References Cited

U.S. PATENT DOCUMENTS

| | | | |
|---|---|---|---|
| 2,584,450 | 2/1952 | Holt et al. | 128/207.14 |
| 3,682,166 | 8/1972 | Jacobs | 128/205.19 |
| 3,788,326 | 1/1974 | Jacobs | 128/207.15 |
| 3,794,026 | 2/1974 | Jacobs | 128/207.15 |
| 3,991,762 | 11/1976 | Radford | 604/119 |
| 4,141,356 | 2/1979 | Smargiassi | 128/204.26 |
| 4,163,450 | 8/1979 | Kirk et al. | 128/204.23 |
| 4,224,939 | 9/1980 | Lang | 128/207.14 |
| 4,248,217 | 2/1981 | Brisson | 128/204.17 |
| 4,305,388 | 12/1981 | Brisson | 128/204.17 |
| 4,459,982 | 7/1984 | Fry | 128/204.23 |
| 4,520,812 | 6/1985 | Freitag et al. | 128/204.25 |
| 4,552,142 | 11/1985 | Hoffman et al. | 128/207.16 |
| 4,565,194 | 1/1986 | Weerda et al. | 128/207.15 |
| 4,569,344 | 2/1986 | Palmer | 128/207.16 |
| 4,589,409 | 5/1986 | Chatburn et al. | 128/203.26 |
| 4,593,687 | 6/1986 | Gray et al. | 128/200.26 |
| 4,611,590 | 9/1986 | Ryschka et al. | 128/204.21 |
| 4,638,539 | 1/1987 | Palmer | 29/157 R |
| 4,677,978 | 7/1987 | Melker | 128/207.29 |
| 4,682,010 | 7/1987 | Drapeau et al. | 128/204.17 |
| 4,682,591 | 7/1987 | Jones | 128/205.11 |
| 4,686,354 | 8/1987 | Makin | 128/204.17 |
| 4,686,974 | 8/1987 | Sato et al. | 128/204.23 |
| 4,796,617 | 1/1989 | Matthews et al. | 128/205.11 |
| 4,805,611 | 2/1989 | Hodgkins | 128/207.14 |
| 4,825,859 | 5/1989 | Lambert | 128/207.14 |
| 4,869,718 | 9/1989 | Brader | 128/207.29 |

FOREIGN PATENT DOCUMENTS 0266051  5/1988  European Pat. Off. ........ 128/201.21

OTHER PUBLICATIONS

Couser, Jr. and Make, "Transtracheal Oxygen Decreases Inspired Minute Ventilation", Am. Rev. Respir. Dis., (1989).

*Primary Examiner*—Edgar S. Burr
*Assistant Examiner*—Aaron J. Lewis
*Attorney, Agent, or Firm*—Dorr, Carson, Sloan & Peterson

[57] ABSTRACT

The present invention provides a system for augmenting ventilation and removing carbon dioxide of a spontaneous-breathing patient and a method of use thereof. The system further allows relaxation of the breathing process thus reducing fatigue of the patient. The system involves providing a high continuous flow of a humidified oxygen/air mixture at a predetermined oxygen content and at a constant flow rate through a transtracheal catheter into the lungs of the patient. The system typically provides an oxygen/air mixture of at least 21 percent oxygen, at a humidity between 80 to 100 percent, and a temperature of 35 to 38 C. The mixture is delivered through the transtracheal catheter at a flow rate of 8 to 20 liters per minute at a back pressure of 2 to 25 psi.

11 Claims, 7 Drawing Sheets

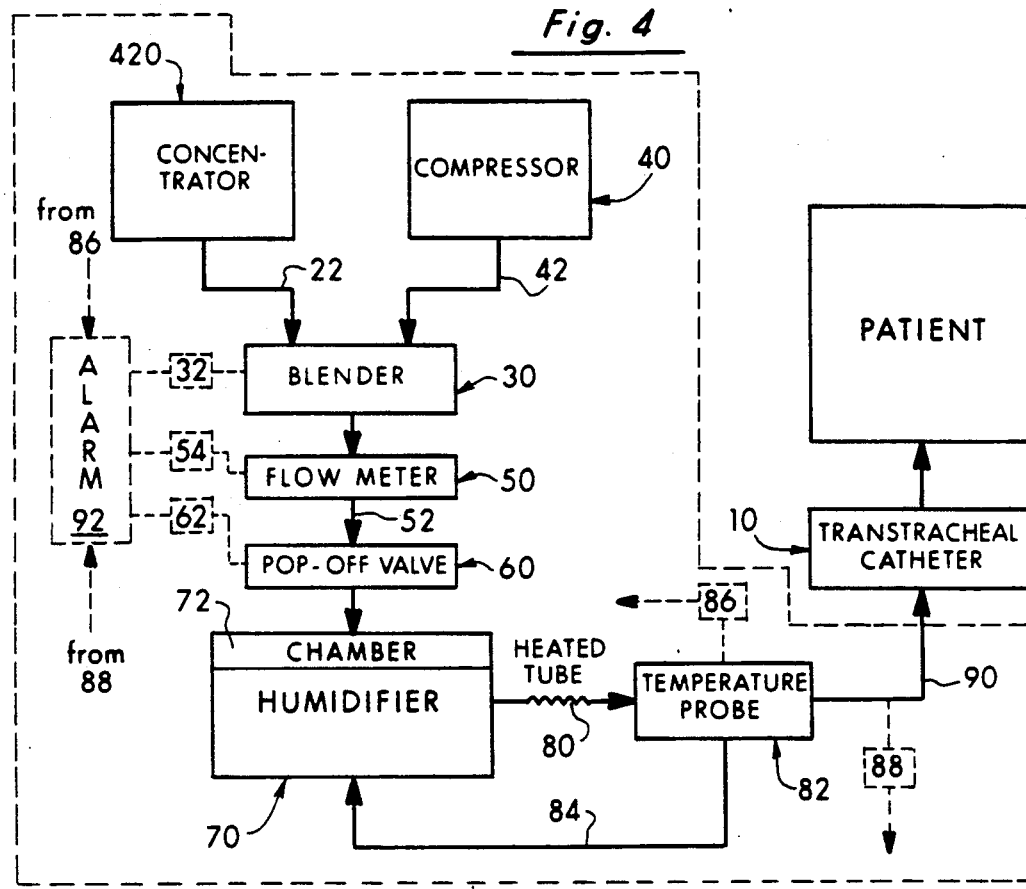
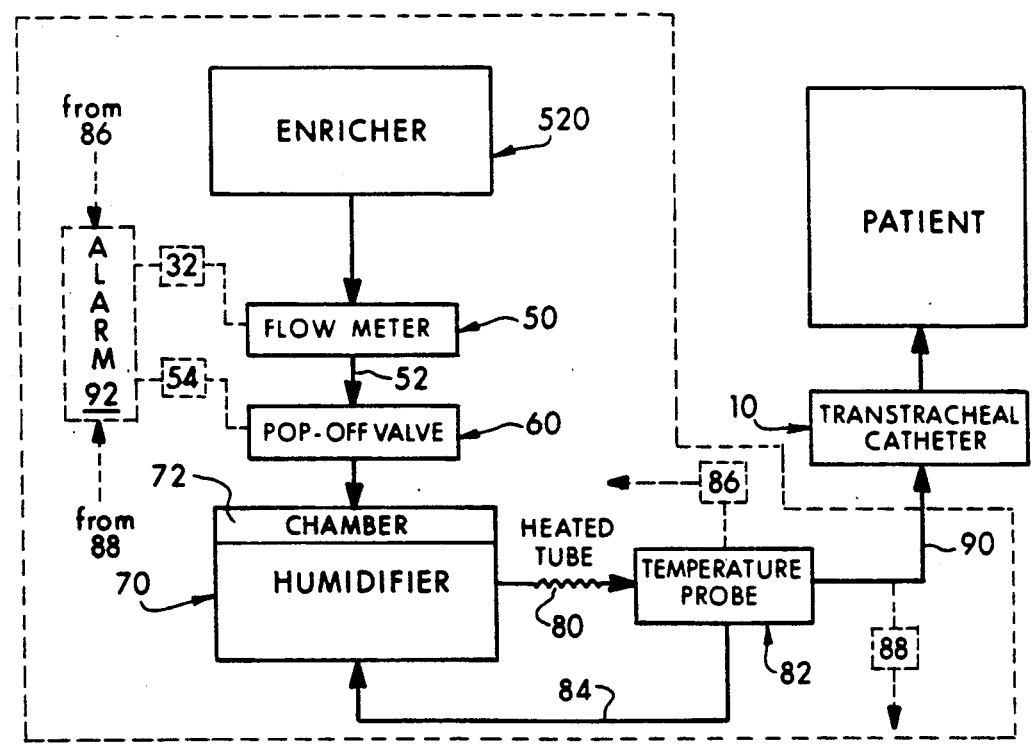

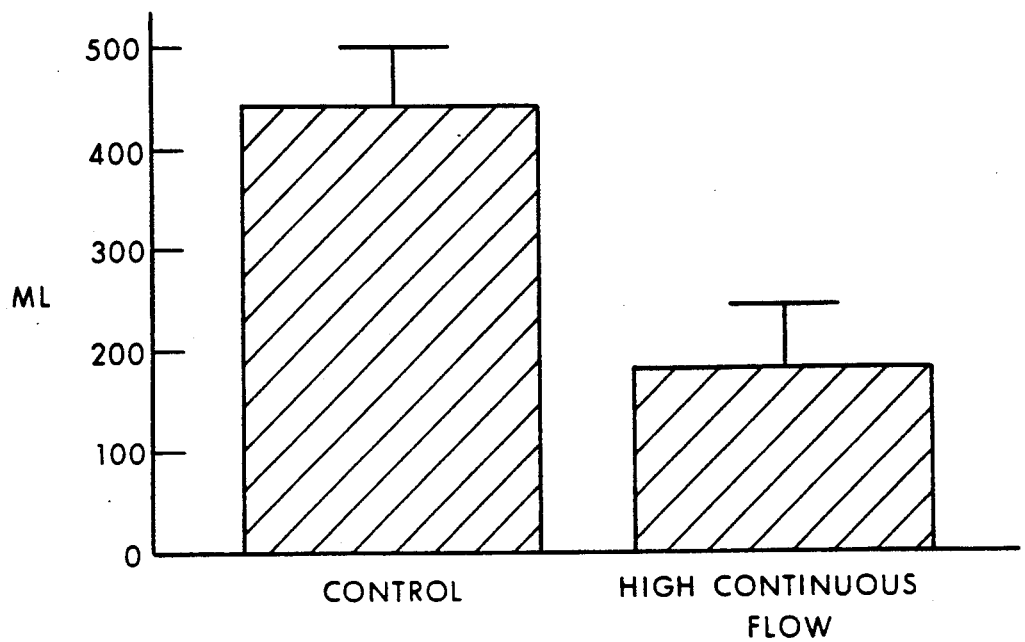
Fig. 6 HIGH CONTINUOUS FLOW INSPIRED TIDAL VOLUME
57% REDUCTION IN TIDAL VOLUME
$P < 0.005$
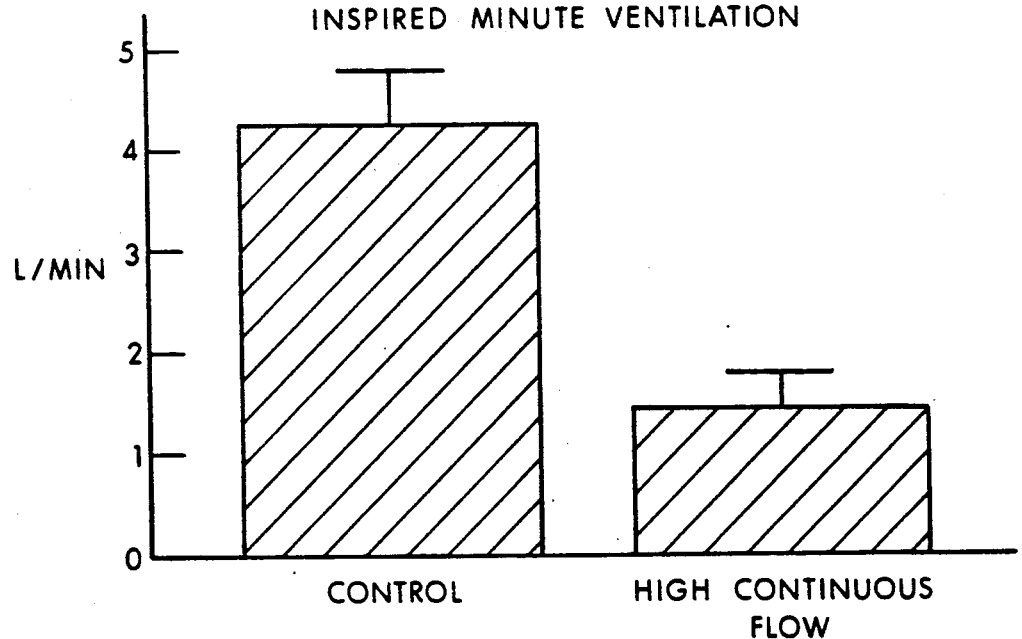
Fig. 7 HIGH CONTINUOUS FLOW INSPIRED MINUTE VENTILATION
65% REDUCTION IN MINUTE VENTILATION
$P = 0.005$

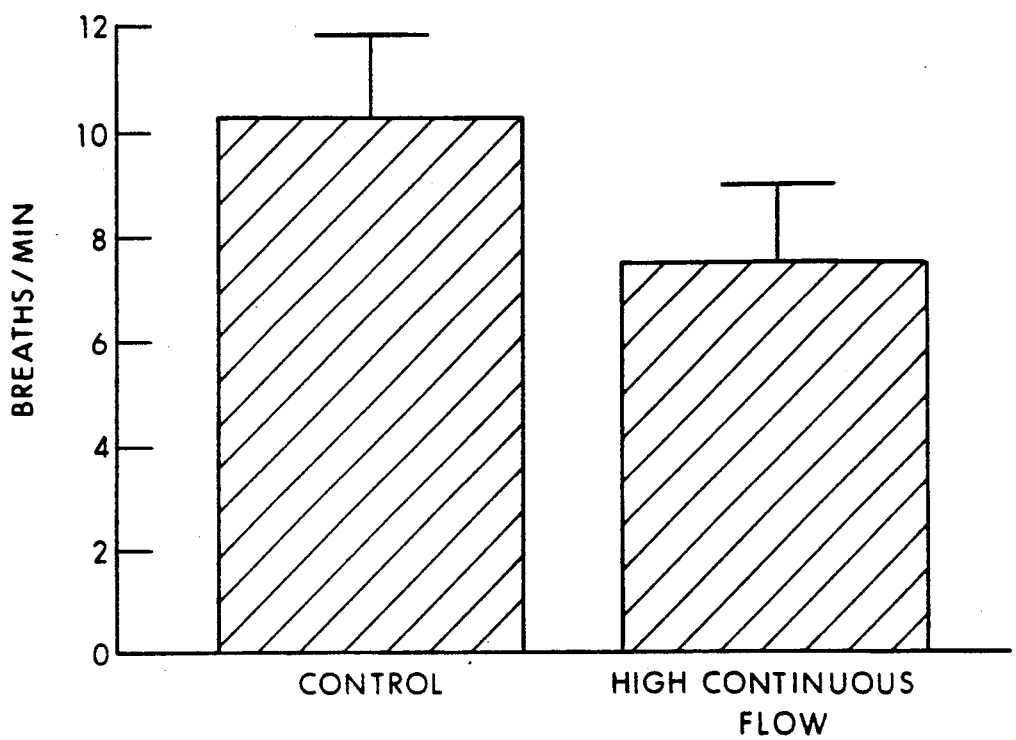
Fig. 8 HIGH CONTINUOUS FLOW RESPIRATORY RATE
26% REDUCTION IN RESPIRATORY RATE
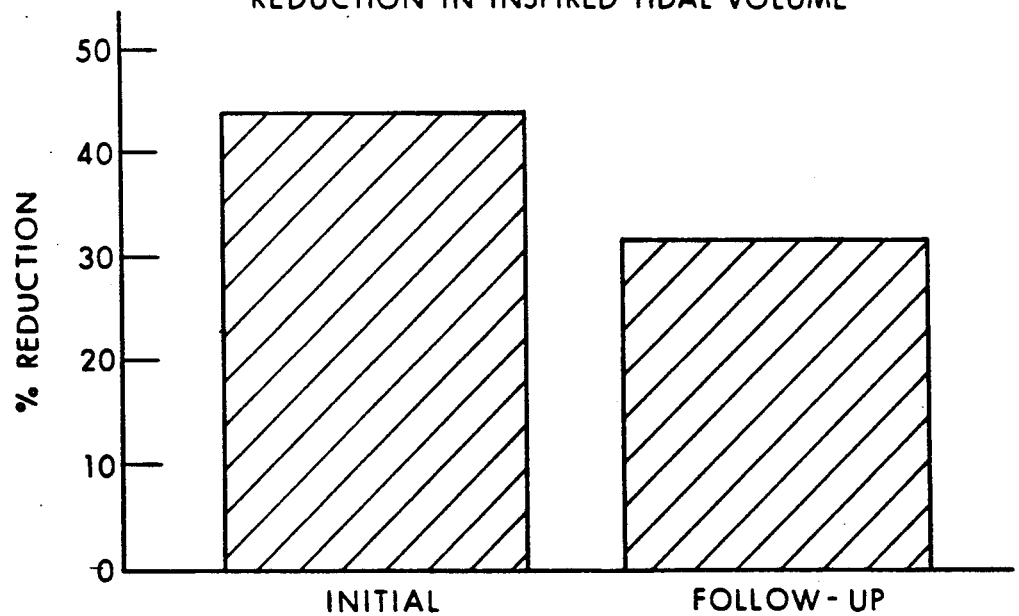
Fig. 9 2 PATIENTS WITH NOCTURNAL CONTINUOUS HIGH FLOW REDUCTION IN INSPIRED TIDAL VOLUME
INSPIRED TIDAL VOLUME WAS REDUCED WITH TRANSTRACHEAL FLOWS OF 10 L/MIN COMPARED TO CONTROLS OF 1-2.5 L/MIN

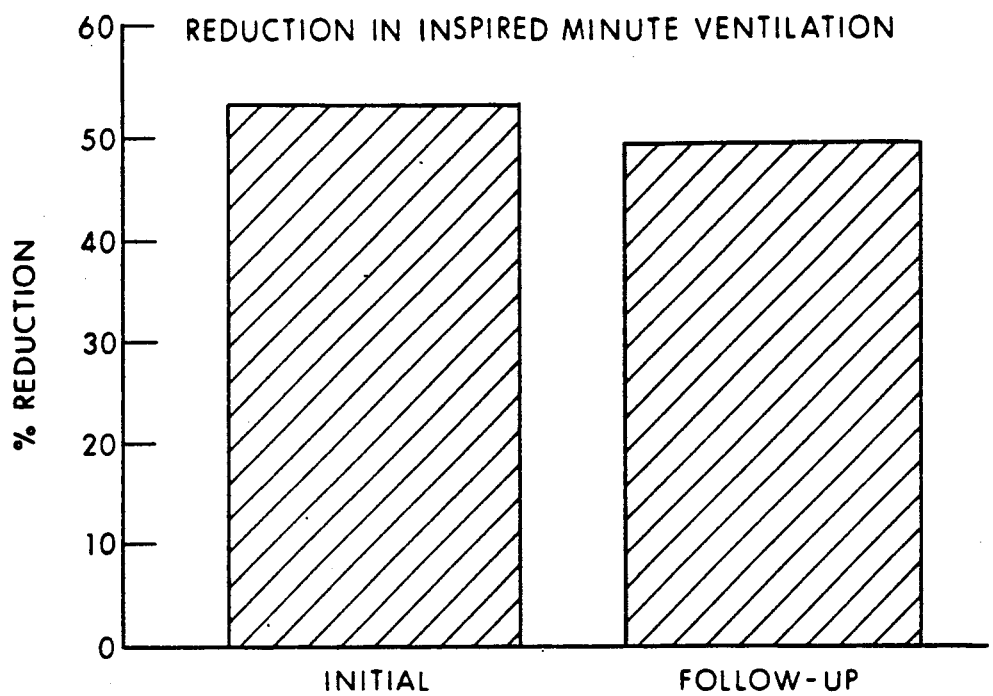

Fig. 10

2 PATIENTS WITH NOCTURNAL CONTINUOUS HIGH FLOW
REDUCTION IN INSPIRED MINUTE VENTILATION

INSPIRED MINUTE VENTILATION WAS REDUCED WITH TRANSTRACHEAL FLOWS OF 10 L/MIN COMPARED TO CONTROLS OF 1-2.5 L/MIN

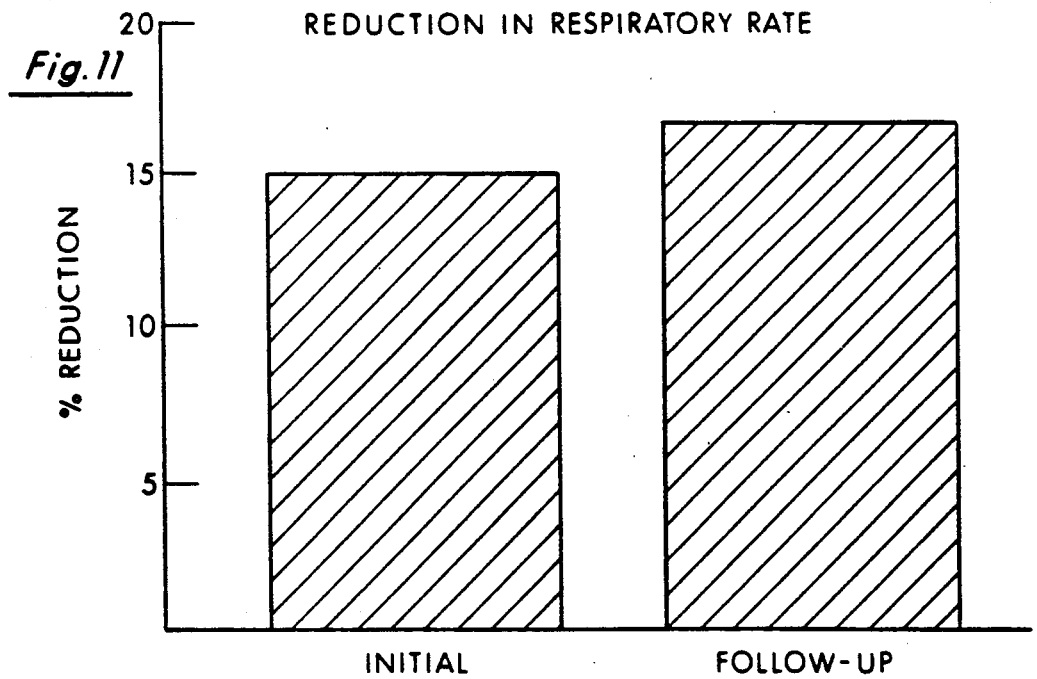

Fig. 11

2 PATIENTS WITH NOCTURNAL CONTINUOUS HIGH FLOW
REDUCTION IN RESPIRATORY RATE

RESPIRATORY RATE WAS REDUCED WITH TRANSTRACHEAL FLOWS OF 10 L/MIN COMPARED TO CONTROLS OF 1-2.5 L/MIN

2 PATIENTS WITH NOCTURNAL CONTINUOUS HIGH FLOW

REDUCTION IN $PaCO_2$ $PaCO_2$ WAS SLIGHTLY REDUCED WITH TRANSTRACHEAL FLOWS OF 10 L/MIN COMPARED TO CONTROLS OF 1-2.5 L/MIN

APPARATUS FOR HIGH CONTINUOUS FLOW AUGMENTATION OF VENTILATION AND METHOD THEREFOR

BACKGROUND OF THE INVENTION

1. Field of the Invention

The present invention relates to the augmentation of ventilation and the removal of $CO_2$ for a medical patient and, more particularly, relates to an apparatus and method for the transtracheal augmentation of ventilation and the $CO_2$ removal through delivery of a high continuous flow of humidified oxygen and air mixture.

2. Statement of the Problem

As defined by Dorland's Illustrated Medical Dictionary (27th Ed. 1988), ventilation in respiratory physiology is the process of exchange of air between the lungs and the ambient air (i.e., inspiration and expiration).

Three basic approaches are available for assisting or augmenting ventilation for a patient. These can be termed external and closed and open delivery systems.

External negative pressure mechanical devices constitute the first type of system. The Drinker respirator, commonly known as the Iron Lung, assists in pulmonary ventilation over long periods of time by enclosing the patient's body, except the head, in a metal tank. Alternating negative and positive pressures within the tank cause the patient to breathe. Oxygen and air is provided to the lungs and the $CO_2$ is removed by these pressures. These types of systems are expensive and immobilize the patients. However, they are designed for patients who cannot entirely self-breathe. Such systems also allow a patient to rest their respiratory muscles by having the mechanical systems do the work of breathing.

Under closed delivery systems, a face mask or an endotracheal tube (i.e., inserted through the mouth or nose and into the trachea) is designed to force oxygen under pressure into the lungs of the patient. Closed delivery systems are air tight, separating the lungs of the patient from the atmosphere. Again, oxygen and air is provided to the lungs and $CO_2$ is removed. Such systems exhibit high inhaling efficiency, but cause irritation or discomfort to the patient through covering of the mouth and nose or through the insertion of a large endotracheal tube into the throat. Closed delivery systems are principally utilized in emergency situations such as intensive care and resuscitation where patients are not able to self-breathe. Such systems are very uncomfortable to patients and are not designed for long term use.

Examples of a closed delivery system are the patents to Jacobs, U.S. Pat. No. 3,788,326 and U.S. Pat. No. 3,682,166 which disclose the use of an occluding balloon to function as a cuff in the throat which minimizes retrograde air leaks during the inflation cycle. This closed delivery system is designed to operate under high pressure (30-100 psi) to physically inflate the lungs.

Open delivery systems supply oxygen into the nostril, the mouth, or the trachea in order to provide oxygen while keeping the lungs of the patient open to the atmosphere. Such systems do not remove $CO_2$ from the lungs. The $CO_2$ is removed by the patient's breathing process. These systems are much more comfortable to the patient than closed systems. For example, the patient is usually permitted to speak, eat or drink freely. Open delivery systems are designed for patients who are capable of self-breathing and they are designed for long term use.

Patients generally prefer the use of a transtracheal catheter over the use of nasal prongs for a number of reasons. Complications of nasal prongs include ear sores, serious otitis media, nasal sores, nasal crusting, nose bleeds, diminished sense of smell and taste, tear duct blockage, chronic dry sore throats, hoarseness, and burns caused by ignition of the nasal prongs. Nasal prongs are often removed because of discomfort, restricted mobility or cosmetic concerns. Finally, nasal prongs are unstable and are often dislodged when the patient sleeps.

An example of a transtracheal approach is the inventors' own transtracheal catheter oxygen delivery system trademarked as "SCOOP" which is manufactured by Transtracheal Systems, Inc., 8775 East Orchard Road, Suite 814, Englewood, Colo. 80111. This approach is disclosed in patent applications: 06/883,409 filed June 13, 1986 and 07/101,173 filed Sept. 28, 1987. The "SCOOP" transtracheal catheter uses a high tech biopolymer of 70-90 shore A durometer which resists kinking and crushing. The internal tubing is radiopaque and is available for adults in 9 cm to 11 cm internal lengths. With an inside diameter of 1.7 and 3.0 mm and an outside diameter of 3.5 mm or less, oxygen flow rates up to 6 liters per minute without exceeding the 2 psi back pressure of conventional delivery systems. The SCOOP transtracheal system provides 24 hour oxygen therapy for patients, contributes to a high quality lifestyle, is low cost, provides superior patient mobility, and is comfortable during nocturnal use.

In "Transtracheal Oxygen Decreases Inspired Minute Ventilation" by Couser, Jr. and Make, Am. Rev. Respir. Dis. (1989), the authors further summarized the benefits of the use of transtracheal oxygen ($TTO_2$) to include: reduction in oxygen requirements, improved compliance, decreased costs, fewer days of hospitalization, improved quality of life, decreased dyspnea, and improved exercise tolerance. The authors investigated the mechanisms for the latter two benefits of decreased dyspnea and improved exercise tolerance by selectively increasing the $TTO_2$ flow rate from 0.5-1.5, 2, 4, and 6 liters/minute. The authors hypothesized that patients receiving $TTO_2$ have decreased inspired minute ventilation and inspiratory work of breathing as the mechanism for improved dyspnea and exercise tolerance.

A need therefore exists for an open delivery system exhibiting the above significant therapeutic attributes that functions in the manner of a closed delivery system to provide artificial and augmented ventilation to a patient whose self-breathing is inadequate, nor dependable, to remove $CO_2$ from the lungs, and to reduce the work of breathing so that the patient's respiratory muscles are not fatigued. A need exists for a long term, home oxygen system that provides nocturnal augmentation of spontaneous ventilation. Furthermore, a need exists for a method of oxygen therapy which improves patient compliance and which can effectively treat some patients who are refractory to nasal cannula delivery.

These needs must be met with a system that does not compromise hemodynamics, that allows for reduction in spontaneous inspired ventilation while maintaining both oxygenation and alveolar ventilation (i.e., elimination of $CO_2$).

3. Results of a Patentability Search

The results of a patentability search directed towards the teachings of the present invention are set forth below:

| U.S. Pat. No. | Inventor | Title |
| --- | --- | --- |
| 3,991,762 | Radford | Aspirating Device for Patient Ventilation Apparatus |
| 4,520,812 | Freitag et al | Method and Apparatus for Controlling a Pressure Level In A Respirator |
| 4,569,344 | Palmer | Aspirating/Ventilating Apparatus and Method |
| 4,593,687 | Gray et al | Endotracheal Catheter |
| 4,638,539 | Palmer | Aspirating/Ventilating Apparatus and Method |
| 4,686,974 | Sato et al | Breath Synchronized Gas-Insufflation Device and Method Therefor |
| 4,805,611 | Hodgkins | Aspirating Device |

An example of transtracheal high frequency jet ventilation (HFJV) is "Method and Apparatus for Controlling a Pressure Level in a Respirator", by Freitag et al., U.S. Pat. No. 4,520,812. Freitag delivers an oscillatory gas stream, at a controlled pressure, from two opposing gas jets through a transtracheal tube. By controlling the pressure and/or frequency of the gas jets, a varying pressure level propagating into the tracheal tube is modulated onto the gas stream. Freitag's apparatus is adjustable within a range of 10 to 1200 pressure pulses per minute with a working pressure between 0.5 to 5 bar.

The patent to Radford, U.S. Pat. No. 3,991,762 entitled "Aspirating Device for Patient Ventilation Apparatus" sets forth a transtracheal catheter used to remove fluid accumulations from the trachea and bronchi of a patient during resuscitation.

The 1986 patent to Gray et al., U.S. Pat. No. 4,593,687 entitled "Endotracheal Catheter" sets forth a method and apparatus for introducing oxygen or a saline solution directly into the trachea in order to facilitate respiration. Gray utilizes a catheter comprising a piece of flexible tubing approximately 1.7 millimeters in diameter and approximately 7.5 centimeters in length with three axially embedded deformed magnetic wires. The distal end of the catheter terminates in an aperture which is smaller in diameter than the inside diameter of the catheter. The proximate end of the catheter terminates in a Leur Lock adapter. The distal end forms a bulbous shape with elliptically shaped slots formed therearound. Insertion of a magnetic probe or stylet causes the bulbous shape to assume a straight and parallel attitude. Under the teachings of Gray, the bulbous shape of the distal end acts to lock or anchor the catheter within the trachea.

The patents to Palmer (U.S. Pat. Nos. 4,638,539 and 4,569,344) relate to an aspirating/ventilating apparatus and method utilizing intensive with a surrounding flexible, collapsible, and preserving film envelope. The Palmer device functions to conjointly ventilate and remove fluid (i.e., aspirate) a patient. Gray utilizes a ventilator that forces air into the lungs of the patient in order to allow the lungs to be adequately expanded and then allows displacement of the air from the patient to be evacuated.

The 1989 patent to Hodgkins, U.S. Pat. No. 4,805,611 and entitled "Aspirating Device" discloses a catheter that is adapted for insertion into the trachea of a patient having at least one aperture for allowing fluid communication between the exterior of the catheter and the passageway contained therein. When the ventilator is used in conjunction with a form of an airway or tube that is inserted into the patient's trachea through the mouth, this is referred to as an endotracheal tube. When a ventilator is used in conjunction with a tube which is inserted into the patient's trachea through an insertion in the patient's neck, this is called a tracheostomy tube. The tracheostomy procedure is preferred because it bypasses and therefore avoids complications of the upper airways. The Hodgkins approach sets forth a tracheostomy tube for removing through suction undesirable secretions from the trachea of a patient.

The 1987 patent to Sato et al., U.S. Pat. No. 4,686,974 sets forth a device and method for insufflating oxygen gas or an anesthetic gas to the respiratory system in synchronism with the patient's breathing. Insufflation of the lungs is the act of blowing air into the lungs for the purpose of artificial respiration. The Sato approach is designed to supply gas only during inhalation periods in synchronism with the breath of the living body in an open type gas insufflation system.

None of the above prior art approaches provide a solution to the problem stated above. None of the approaches uncovered in the patentability search provides an open delivery system which exhibits significant patient comfort, yet functions as a closed delivery system to provide augmented ventilation and $CO_2$ removal to a patient who cannot fully self-breathe and with long term nocturnal support.

4. Solution to the Problem

The present invention provides a solution to the above-identified needs by utilizing a small diameter transtracheal catheter such as the inventors' "SCOOP" transtracheal catheter and by delivering a high continuous flow (HCF) of an oxygen/air mixture at controlled pressure, humidity, and temperature on a continuous basis into the lungs of a patient with inadequate breathing to augment ventilation and to facilitate the removal of $CO_2$.

The present invention is designed as a long term, home oxygen system that provides for nocturnal augmentation of spontaneous ventilation. The present invention also offers a choice for patients who have inadequate breathing due to respiratory failure resulting from problems with shortness of breath, $CO_2$ removal, and respiratory muscle strength.

The present invention may also be used in an intensive-care unit for hospitalized patients requiring augmentation of spontaneous ventilation. The invention may particularly be advantageous for patents requiring long term stays in intensive care.

While the present invention permits nocturnal augmentation, oxygenation and alveolar ventilation is maintained even though spontaneous inspired ventilation decreases. This is important for patients who cannot fully self-breathe as it allows for the patient's breathing muscles to relax and to become rested. In other words, the present invention provides respiration through high volume continuous flow through the lungs without forcing pulses of high pressure air into the lungs to simulate breathing as in closed delivery systems or through the use of alternating positive and negative air pressure external to the body in order to simulate breathing as found in iron lungs.

The present invention is also useful for patients suffering from sleep apnea, which is a condition causing transient attacks of obstruction of the throat and/or failure of automatic control of respiration, resulting in alveolar hypoventilation. This condition becomes more pronounced during sleep. Nocturnal use of the present invention is an aid against sleep apnea.

Finally, the present invention has a further advantage for those patients who are capable of some sustained self-breathing in that the same transtracheal catheter may be used for day time use in a standard transtracheal oxygen supply system when the patient is capable of self-breathing and for nocturnal use in the system of the present invention when the patient has respiratory failure, retention of $CO_2$, and/or the inability to sustain the work of breathing.

SUMMARY OF THE INVENTION

The present invention provides a comfortable, lifestyle enhancing system for the transtracheal augmentation of ventilation for a patient which facilitates the removal of $CO_2$ and the resting of respiratory muscles. The system comprises a source of an oxygen/air mixture having at least twenty-one percent oxygen as a component thereof. The oxygen/air mixture is maintained in the 80 to 100 percent humidity range at a temperature of 35 to 38 degrees C. The oxygen/air mixture is then delivered through a transtracheal catheter in a flow range of 8 to 20 liters per minute at a back pressure of 2 to 25 psi.

The method of the present invention is to provide an oxygen/air mixture of at least 21 percent oxygen, at a humidity between 80 to 100 percent, and a temperature of 35 to 38 degrees C. This oxygen/air mixture is then continuously delivered through the transtracheal catheter at a flow rate of 8 to 20 liters per minute at a back pressure of 2 to 25 psi.

A patient is able to use the system and method of the present invention to improve his or her lifestyle by using it at home and comfortably through the night.

BRIEF DESCRIPTION OF THE DRAWING

FIG. 4 is a block diagram of a second embodiment of the high continuous flow system of the invention.

FIG. 5 is a block diagram of a third embodiment of the high continuous flow system of the invention.

FIG. 6 is a chart showing the reduction in tidal volume of the animal clinical study.

FIG. 7 is a chart showing the reduction in minute ventilation of the animal clinical study.

FIG. 8 is a chart showing the reduction in respiratory rate of the animal clinical study.

FIG. 9 is a chart showing the reduction in inspired tidal volume of the human clinical study.

FIG. 10 is a chart showing the reduction in inspired minute ventilation of the human clinical FIG. 11 is a chart showing the reduction in respiratory rate in the human clinical study.

GENERAL DESCRIPTION OF THE PREFERRED EMBODIMENT

Figure 1:
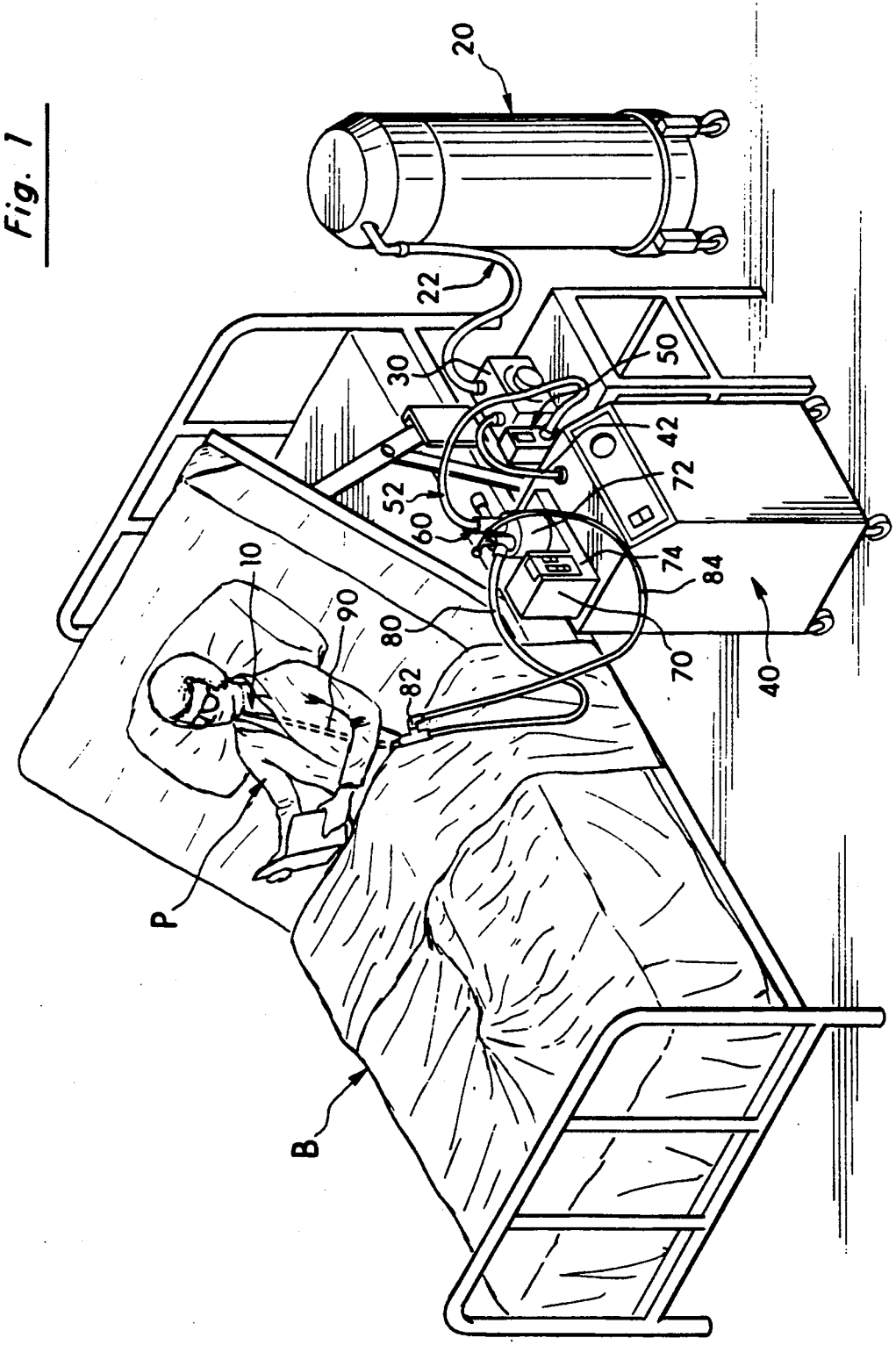
FIG. 1 is an overview of the system of the present invention being used in a home care environment.

The present invention is a system for the transtracheal augmentation of ventilation including alveolar ventilation and resting of the respiratory muscles for a patient requiring respiratory assistance and the method for the use of the system. The system is intended for long term use not only in a hospital situation but also for long term use in a home care environment. A preferred embodiment of the current invention is illustrated in FIG. 1. The embodiment illustrated in FIG. 1 is used in a home care environment by a patient P without the need of costly hospital care and supervision or home nurse support. The system as shown in FIG. 1 utilizes various commercially available components.

In FIG. 1, a patient P is reading in a bed B. The patient has a transtracheal catheter 10 inserted into his or her trachea. An oxygen/air mixture is delivered through the catheter 10 from the equipment of the present invention. A liquid oxygen tank 20 provides a source of oxygen and is connected through tube 22 to a blender 30. A compressor 40 provides a source of air and is also connected to blender 30 through tube 42. The blender 30 delivers the oxygen/air mixture to a flow meter 50 which delivers a regulated flow through tube 52 to a pop-off valve 60. The pop-off valve 60 connects to a humidifier 70 which outputs the oxygen/air mixture through a heated tube 80 to tube 90 which connects directly to catheter 10. A temperature probe 82 is positioned between tubes 80 and 90 and an electrical signal is fed back over lead 84 to the humidifier 70 which controls the temperature of the heated tube 80.

In the preferred embodiment, the liquid oxygen from tank(s) 20 and the air from compressor 30 are mixed together by blender 30 in a preselected ratio. The oxygen/air mixture is then delivered through flow meter 50 which regulates the flow to the high continuous flow rate of 8 liters/minute or more of the present invention. The oxygen/air mixture is then delivered into the humidifier 70 which maintains the humidity at a desired level and then through a heated tube 80 which maintains the temperature at a selected value near the patient's body temperature. The oxygen/air mixture is then delivered through the transtracheal catheter 10 into the lungs of patient P.

Under the teachings of the present invention, a ventilation augmentation system is provided which can be used in the home or hospital for long term therapy. It is to be expressly understood that the equipment and ranges set forth in the following are preferred embodiments and that variations and modifications can be made thereto which will still fall within the teachings of the present invention. The high continuous flow rates achieved by the present invention require that the humidity and temperature of the oxygen/air mixture be controlled so as to minimize discomfort, drying, and irritation to the patient.

The individual components of the system of the present invention are separately available but have not been used in a system such as in the present invention to provide augmentation of ventilation for a patient, removal of $CO_2$ from the lungs of a patient, patient's respiratory muscles to relax. A more detailed description of the system including the method of use is discussed below.

DETAILED DESCRIPTION OF THE PREFERRED EMBODIMENT

Figure 3:
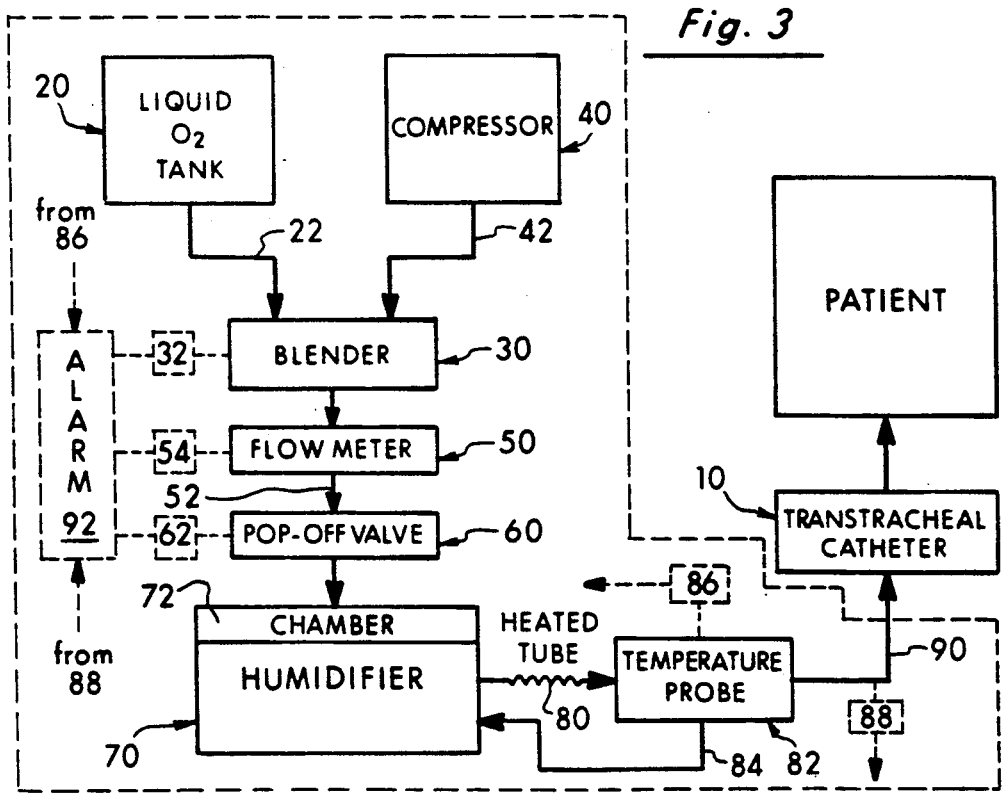
FIG. 3 is a block diagram of one embodiment of the high continuous flow system of the invention.

The basic system of FIG. 1 is outlined in the block diagram of FIG. 3. Each of the individual components will be discussed in more detail below.

Liquid oxygen from tank 20 is mixed with air from compressor 40 in blender 30. The oxygen and air is mixed to approximately a 40 percent oxygen blend to maintain adequate blood oxygen although any mixture in a range of at least 21 to 100 percent oxygen could be so utilized. Transducer 32 monitors the oxygen content of the mixture exiting the blender 30. Should the oxygen content fall outside a desired range, the transducer 32 triggers a signal to alarm 92 which notifies the patient or others of the incorrect oxygen content so that the content can be adjusted before harm occurs to the patient. Alarm 92 can be local to the patient or suitably remote.

The blended oxygen/air mixture leaves the blender 30 and goes into a flow meter 50 which is adjusted to the desired flow rate for the patient, normally in a flow range from 8 to 20 liters per minute. Transducer 54 is connected to the flow meter 50 to monitor the flow rate of the mixture exiting the flow meter. If the flow falls below or rises above the preselected flow, the transducer 54 triggers a signal to the alarm 92 so the flow can quickly be adjusted.

The air is directed from the flow meter 50 through a flexible tube 52 into a pop-off valve 60. The pop-off valve 60 regulates the back pressure of the flow of the oxygen/air mixture in a preferred range of 2 to 25 psi. Transducer 62 is connected to the pop-off valve 60 to monitor the back pressure of the mixture. If the pressure falls below the preselected range, i.e., the mixture is not flowing or if the pressure rises too high, the transducer 62 triggers the alarm 92 so the system can be properly adjusted.

The mixture is directed from the pop-off valve into a humidifier 70 which maintains the mixture at a selected humidity in order to prevent the mixture from drying out the patient's trachea and lungs. One such humidifier, as will be more fully described below, regulates the humidity of the mixture by maintaining the temperature of the mixture at a desired temperature, such as the patient's body temperature. The mixture flows from the humidifier 70 through a heated tube 80. The temperature of the mixture in the tube 80 is monitored by a temperature probe 82 which is connected by a feed back 84 coupled to the humidifier 70 and heated tube 80 to maintain the mixture temperature at the desired value. The probe 82 is connected as close as practically possible to the transtracheal catheter so the mixture can be monitored as near the patient as is feasible. A transducer 86 coupled to the tube monitors the temperature of the mixture as well. Should the temperature fall below or rise above the selected range, the transducer 86 triggers the alarm 92 so the system can be adjusted. Another transducer 88 monitors the humidity range of the mixture to trigger the alarm should the humidity of the mixture fall outside the selected range.

The mixture then flows through tube 90 and into a transtracheal catheter 10 which has been inserted into the patient P.

The block diagram in FIG. 3 is typified by the set up of the system illustrated in FIG. 1. Each of the components are presently commercially available. The present invention is not meant to be limited by the identification of the particular components and other components can readily be used without departing from the scope of the invention.

The liquid oxygen tank(s) 20 is readily obtainable from medical supply houses, such as the "LIBERATOR 53" liquid oxygen tank from CRYOGENIC ASSOCIATES, New Prague, Minn. Liquid oxygen is preferable over high pressure oxygen cylinders due to the ease of handling and cost. The liquid oxygen is delivered by flexible tubing 22 into blender 30, such as the "BIRD 3800 MICROBLENDER", manufactured by Bird Products Corporation, Palm Springs, Calif.

The oxygen is mixed in precise concentrations in blender 30 with air delivered through flexible tubing 42 from a medical air compressor 40, such as the "6500 AIR COMPRESSOR" also manufactured by Bird Products Corporation. Normally a concentration of 40 to 50% oxygen is desired although a range of at least 21 percent oxygen to 100 percent could be utilized. The blender 30 has a control for setting the desired blend of oxygen to a predetermined value as determined by the physician or technician attending the patient. The setting will be such to maintain the proper blood oxygen level.

The transducers and alarms used to monitor the oxygen content, the flow rate, the pressure, the temperature and the humidity of the mixture are of types generally used in the medical field.

Attached to the blender 30 is a flow meter 50 which receives the blended oxygen/air mixture. The flow meter 50 is adjustable to regulate the flow of the mixture from 2 to 20 liters per minute. In this system, the desired range is typically 8 to 20 liters per minute. The mixture flows from the flow meter 50 through flexible tubing 52 into a pop-off valve assembly 60 which regulates the back pressure of the mixture. The valve is adjustable to regulate the back pressure in a range of 2 to 25 psi. Should the pressure build up over 25 psi, the pop-off will bleed the excessive pressure of the mixture. The pop-off valve is mounted directly to the chamber 72 of the humidifier 70.

One such chamber is the "MR300" humidifying assembly (which can be disposable or non-disposable) by Fisher & Paykel, Auckland, New Zealand. Other conventional chambers could easily be used as well. The chamber 72 is mounted on a humidifier heater base 74, such as the "MR620" Dual Servo Anesthesia Humidifier Heater Base by Fisher & Paykel. This particular heater base is designed to limit the variation of the set temperature and humidity.

The mixture enters the humidifier 70 from the pop-off valve 60 and exits at a preferred humidity range of 80 to 100% with a preferred temperature range of 35 to 38 degrees Centigrade. This is approximately the body temperature of the patient P. Maintaining the temperature and humidity at these ranges prevents the mixture from drying out the trachea and lungs of the patient. To maintain this temperature range, a heated wire is placed in the tube 80 exiting from the humidifier chamber 72. At the end of the tube 80 is a coupling containing temperature probe 82 which connects the tube 80 to the external hose 90 of the catheter system 10. The temperature probe 82 as well as the transducers 84 and 86 are mounted as near the patient P as is practically possible without being obtrusive. This enables the mixture to be closely monitored as it enters the patient P. The temperature probe 82 monitors the temperature of the flowing mixture. The probe 82 is fed back to the heater base 74 and the heated tube 80 to maintain the temperature of the mixture.

The components as described to this point are of a size and nature to be easily mounted on a wheeled cart. The related compact size of the system allows the system to be easily moved in either a home or hospital setting and is unobtrusive in the patient's home.

Figure 2:
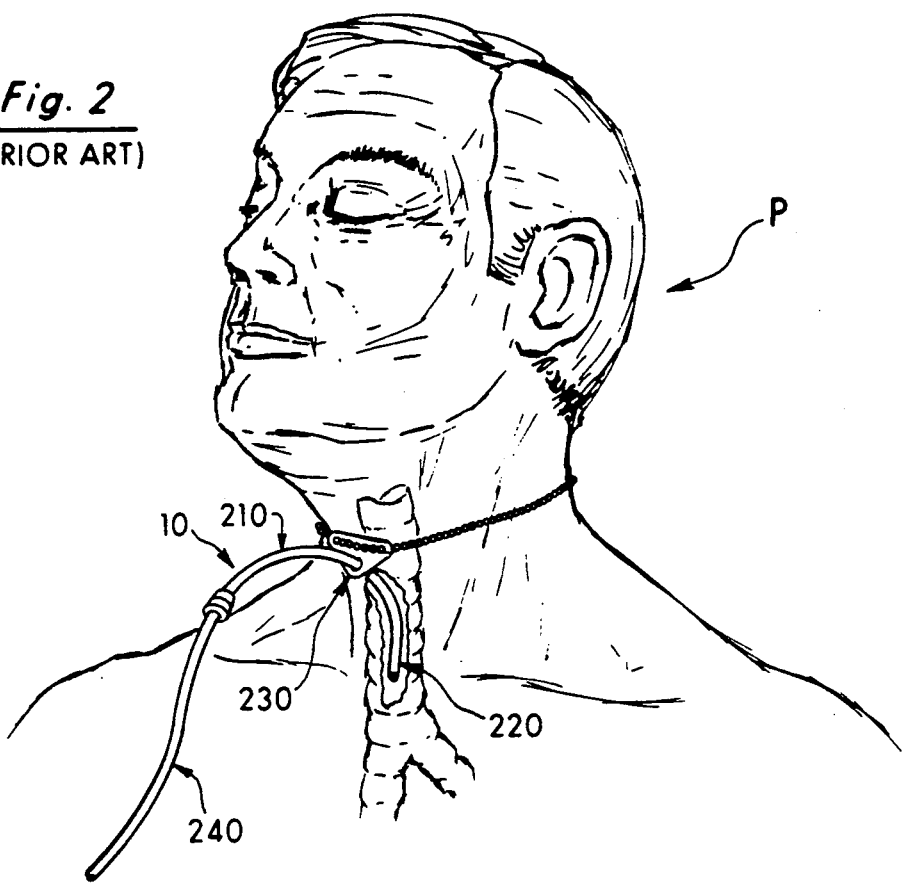
FIG. 2 is a view of a prior art transtracheal catheter.

A transtracheal catheter system 10 is connected to the hose 90 such as the "SCOOP" oxygen hose to deliver the oxygen/air mixture to the patient's lungs. A preferred transtracheal catheter system is the "SCOOP" transtracheal system. This system is illustrated in FIG. 2. The catheter tube 210 is inserted through a surgically formed opening through the trachea in the neck of the patient. The catheter 210 includes a 9 french flexible tube 220 having a durometer of between 70 to 90 Shore A. The catheter tube 220 has an external diameter substantially less than the cross-sectional area of the trachea, ranging from 3.5 millimeters or less. The inside diameter of the tube 220 ranges from 1.7 to 3.0 millimeters. The tube 220 is designed to be flexible to be easily inserted and shaped within the trachea of the patient, yet rigid to maintain its shape and to prevent collapsing of the tube. The tube is inserted so that the distal end of the tube is located just above the carina to direct the flow of the mixture evenly into the right and left bronchus of the patient. The catheter tube 220 is held in place by an abutment structure 230 which is held by a collar around the patient's neck. External hose 240 connects the catheter tube 220 to the coupling 82 through which the mixture is supplied.

The system of the current invention for transtracheal augmentation of ventilation is not limited to use with the "SCOOP" transtracheal catheter system but may also utilize other transtracheal catheters as well.

Other variations in the components of the system include replacing the liquid oxygen tank 20 with an oxygen concentrator 420 as illustrated in FIG. 4. The concentrator 420, such as commercially available by Mountain Medical Equipment, Incorporated, Littleton, Colo., uses a molecular sieve material to separate the oxygen from the rest of the air by the process of adsorption. This eliminates the cost of replacing and refilling the liquid oxygen tanks. The remaining apparatus of FIG. 4 is equivalent to the above-described system for FIG. 3 and is numbered in the same sequence.

Another variation is illustrated in FIG. 5. This system uses an oxygen enricher 520 in place of the liquid oxygen tanks and the air compressor. The enricher 520 uses a permeable plastic membrane to separate oxygen and water vapor from the rest by differences in gas diffusion rates. The units, such as the OECO high-humidity system manufactured by the Oxygen Enrichment Company, delivers a constant 40% oxygen/air mixture directly to the flow meter without the need of the blender. The remaining apparatus of FIG. 5 is equivalent to the above-identified system for FIG. 3 and is numbered in the same sequence.

The system of the present invention is designed to be used in a hospital setting as well, particularly in intensive care units. Instead of liquid oxygen tanks and air compressors, bulk supplies (not shown) can be readily utilized directly to the blender.

The system of the present invention is not meant to be limited by the description of the above apparatus. Other variations in components and types of components are considered to be within the scope of the inventive concept embodied by the system and method of the present invention.

The method of the current invention utilizes apparatus such as that described above. An air/oxygen mixture is supplied, with a fractionally inspired oxygen content of at least 0.21 to 1.00 and preferably about 0.4. The mixture is supplied to the patient at a constant flow rate of 8-20 liters per minute, preferably at about 10 liters per minute. The flow is regulated at a back pressure of between 2-25 psi. In order to prevent the trachea and lungs of the patient from drying out as well as to retard the build-up of mucous in the tubes, the mixture is maintained at a humidity range of 80 to 100% and a temperature corresponding to the body temperature of the patient, preferably 35 to 38 degrees Centigrade.

The mixture is supplied to a transtracheal catheter, such as the above-described "SCOOP" catheter. This directs the continuous flow of the mixture directly and evenly into the lungs of the patient without the complications of a mask, endotracheal tube or nasal prongs.

Each of the above steps is important in the present invention. By supplying the oxygen/air mixture at a fractional inspired oxygen content of at least 0.21 to 1.00 and by controlling the flow rate from 8 to 20 liters per minute, the patient is able to reduce the labor and fatigue involved in spontaneous breathing. The augmentation still allows the patient to remove the excess carbon dioxide levels without the need of mechanical assistance or closed ventilation systems which force breathing. The present invention unlike those prior approaches permits the patient to spontaneously breathe at any time.

The control of the humidity and temperature of the mixture alleviates the trachea and lungs of the patient from drying out as well as retarding the plugging of the catheter and tube from mucous. The use of the pop-off valve prevents the system from overloading should the tubes become blocked or kinked or should the system malfunction in some manner.

The transtracheal catheter allows the use of an open delivery system without the need of nasal prongs. Further, the use of a transtracheal catheter allows high flow rates without obstruction of the trachea.

The use of the present invention for augmentation of ventilation and for removal of carbon dioxide is accomplished by the delivery of a high continuous flow of an oxygen/air mixture through a transtracheal catheter system. By using the transtracheal system, the benefits of an open system is realized, allowing the patient to speak, eat and drink freely as well as to more comfortably sleep with nocturnal augmentation.

This method aids in the ventilation of a patient suffering from respiratory problems such as chronic hypercarbic respiratory failure, the obstructed upper airway of sleep apnea and other respiratory problems where alveolar ventilation is a problem.

The present invention is not meant to be limited by the above-discussion of the method of augmentation of ventilation and removal of carbon dioxide of a patient. Other variations in the steps and in the uses of the present invention are considered to be well within the scope of the invention concept of the present invention. The above described system and method are merely for descriptive purposes and are not meant to limit the scope of the present invention.

CLINICAL STUDIES

The High Continuous Flow (HCF) procedure of the present invention has been tested in two clinical studies, first in canine models using lightly anesthetized spontaneous breathing animals and secondly, in nocturnal augmentation of spontaneous ventilation in patients with severe chronic hypercarbic respiratory failure, that is patients with excess carbon dioxide in their blood due to insufficiency of ventilation.

In the canine study the concerns addressed were: (1) whether the High Continuous Flow procedure of the present invention could be administered via a standard transtracheal oxygen catheter; (2) are the hemodynamics (i.e., the physiological aspects of the blood circulation) compromised by the use of the HCF procedure; (3) is there a reduction in spontaneous inspired ventilation with the HCF procedure; and (4) if there is a reduction in spontaneous inspired ventilation, are both oxygenation and alveolar ventilation maintained.

In the human study, the primary concerns tested were whether similar results are obtained in spontaneous inspired ventilation and arterial blood gases as seen both with short-term and long-term treatment of patients with hypercarbic respiratory failure and whether long-term nocturnal HCF can be safely and practically administered in the home.

1. ANIMAL STUDIES a. Procedure

Nine canines having an average weight of 28 kilograms were lightly anesthetized with pentobarbital to simulate a sleeping patient model. A 9 french "SCOOP" transtracheal catheter was inserted in each canine via the cricothyroid membrane. An 8 french pressure monitoring catheter was also inserted in each canine so the tip was six centimeters beyond the "SCOOP" catheter tip via the cricothyroid membrane to monitor the airway pressure of the animals. Inflatable cuff endotracheal tubes were placed above the catheter tips in the glottis with a one-way valve and a pneumotach attached. This allowed the inspiratory flow and volume to be recorded. The position of the catheters and tubes were confirmed by bronchoscopy. An indwelling femoral arterial catheter and thermodilution pulmonary arterial catheter were inserted.

Immediately after a thirty minute control period of spontaneous breathing, each animal randomly received the following experimental conditions. The High Continuous Flow procedure was administered by the above-described apparatus at a flow rate of ten (10) liters per minute. The fraction of inspired oxygen was set at forty per cent (40%) to simulate normally inspirated air in spontaneous breathing.

b. Results (i) Inspired Tidal Volume: The inspired tidal volume during the control period (normal breathing) was approximately 450 milliliters while the inspired tidal volume during the High Continuous Flow period was approximately 200 milliliters as shown in FIG. 6. This amounts to a decrease of 60%. This is a highly statistical significant event relating to the reduction of depth of breathing necessary while retaining blood oxygen.

(ii) Inspired Minute Ventilation: The inspired minute ventilation (tidal volume × respiratory rate) observed during the control period was approximately 4.5 liters per minute while during the High Continuous Flow period it was 1.5 liters per minute, a reduction of 66% in minute ventilation as shown in FIG. 7. This is also a significant event indicting that less depth and rate of breathing is necessary during the High Continuous Flow to maintain the blood oxygen.

(iii) Respiratory Rate: The respiratory rate during the control period was approximately 11 breaths per minute while during the High Continuous Flow procedure it was 8 breaths per minute as shown in FIG. 8. This was a reduction of 26% in respiratory rate which is not considered a significant event.

(iv) Carbon Dioxide Level: The $PaCO_2$ levels showed no significant change, indicating breathing remained normal during the HCF Procedure.

(v) Oxygen Level: The $PaO_2$ levels showed an increase compared with the control period.

(vi) Other Test Indications: There were no significant changes compared with the control period and the HCF period in the systemic arterial pressure, the heart rate, the pulmonary arterial pressures the $P_{AW}$ or thermodilution cardiac output.

c. Conclusions

From these results of the High Continuous Flow test period compared to the control period the following conclusions are reached:

(i) There were no complications during the HCF Procedure.

(ii) The hemodynamics were not comprised during the HCF Procedure.

(iii) Spontaneous inspired ventilation decreased during the HCF Procedure.

(iv) Alveolar ventilation ($PaCO_2$) was maintained.

(v) Oxygenation improved.

2. HUMAN STUDIES a. Procedures

Two patients suffering from severe chronic hypercarbic respiratory failure were studied over a five month period. The patients underwent nocturnal augmentation of ventilation with High Continuous Flow with the above-described apparatus. The patients prior to using the High Continuous Flow procedure were normally breathing 1-2.5 liters per minute of pure oxygen diluted by what is inhaled. The High Continuous Flow Procedure used transtracheal flows of 10 liters per minute, back pressure of 2-25 psi, humidity of 80-100 percent, and temperatures of 35 to 38 degrees C.

b. Results (i) Inspired Tidal Volume: The inspired tidal volume initially was reduced 45% with a reduction of 30% over a long term period as shown in FIG. 9.

(ii) Inspired Minute Ventilation: The inspired minute ventilation initially was reduced 55% with a reduction of 50% over a long term period as shown in FIG. 10.

(iii) Respirator Rate: The respiratory rates of the patients was initially reduced 15% with a reduction of 18% over a long term period as shown in FIG. 11.

Figure 12:
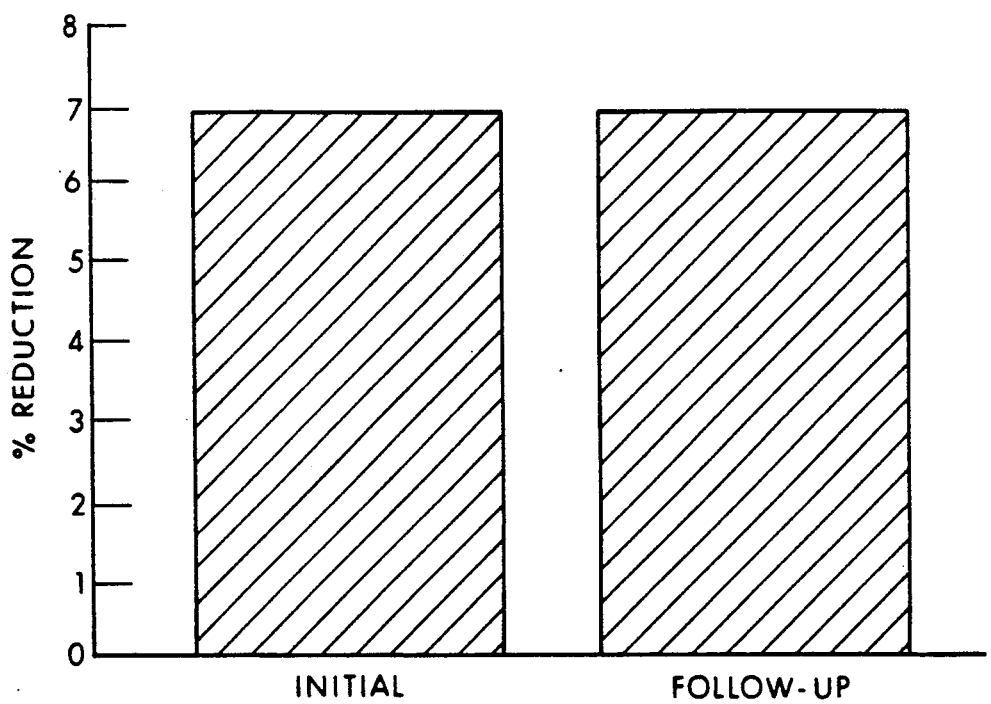
FIG. 12 is a chart showing the reduction in carbon dioxide levels in the human clinical study.

(iv) Alveolar Ventilation Levels: The $PaCO_2$ levels (Alveolar Ventilation) were reduced by approximately 7% as shown in FIG. 12.

c. Conclusions

The following conclusions were reached by comparisons of the two patients prior to and during the High Continuous Flow Procedure:

(i) There were no complications using nocturnal augmentation of ventilation with High Continuous Flow on patients with severe chronic hypercarbic respiratory failure during the testing period.

(ii) Patient acceptance was high with reduced dyspnea on High Continuous Flow. The patients were able to breathe with less difficulty and the muscles involved with the breathing process were thus more relaxed.

(iii) Compared to the control period, inspired spontaneous ventilation was reduced.
(iv) Compared to the control ventilation was maintained.
(v) The test results persisted over time.

SUMMARY

In conclusion, the present invention sets forth a simple, easily manufactured and used system. The system and method of the present invention provides augmentation of ventilation and removal of carbon dioxide by the transtracheal delivery of a high continuous flow of an oxygen and air mixture into the lungs of the patient. It allows a patient to relax his or her respiratory muscles while preserving spontaneous breathing. This is done in such a manner so to improve the care and lifestyle of a patient. While the specific embodiments and ranges have been shown and described to illustrate the principles of the present invention, it will be understood that the invention may be embodied otherwise without departing from such principles.

We claim:

1. An open delivery system for continuous flow augmentation and ventilation of a patient, said system comprising:
    means for maintaining the lungs of a patient open to the ambient atmosphere including means for allowing a patient to breathe spontaneously thereby removing carbon dioxide:
    means for providing a continuous flow of an oxygen/air mixture of at least twenty-one percent oxygen,
    means connected to said providing means for selectively controlling said continuous flow of said oxygen/air mixture at a constant flow rate in a flow rate of eight to twenty liters per minute,
    means connected to said controlling means for regulating the pressure of said oxygen/air mixture generated by said providing means in a back pressure range of two to twenty-five pounds per square inch,
    means connected to said regulating means for maintaining the humidity of said oxygen/air mixture in a humidity range of eighty to one hundred percent, said maintaining means being further capable of maintaining the temperature of said oxygen/air mixture in a temperature range of thirty-five to thirty-eight degrees Celsius, and
    a transtracheal catheter connected to said maintaining means for continuously delivering said oxygen/air mixture into the trachea of said patient.

2. The system of claim 1 wherein said providing means comprises:
    means for storing liquid oxygen,
    an air compressor for compressing air, and
    means connected to said storing means and to said air compressor for adjustably blending said oxygen from said storing means with air from said air compressor to form said oxygen/air mixture.

3. The system of claim 1 wherein said providing means comprises:
    a concentrator for generating oxygen,
    an air compressor for compressing air, and
    means connected to said generating means and to said air compressor for adjustably blending said oxygen from said generating means with air from said air compressor to form said oxygen/air mixture.

4. The system of claim 1 wherein said providing means is an enricher.

5. The system of claim 1 wherein said controlling means is a flow meter.

6. The system of claim 1 wherein said regulating means is a pop-off valve.

7. The system of claim 1 wherein said maintaining means comprises:
    a humidifier,
    a tube having one end connected to said humidifier for carrying said oxygen/air mixture,
    a heated wire in said tube for heating said oxygen/air mixture,
    a temperature probe at the other end of said tube for measuring the temperature of said oxygen/air mixture as it leaves said tube, and
    means connected to said heated wire and to said temperature probe for adjustably setting the temperature of said oxygen/air mixture in said temperature range.

8. The system of claim 1 wherein said transtracheal catheter comprises a catheter having an outside diameter of less than 3.5 millimeters.

9. The system of claim 1 wherein said transtracheal catheter comprises a catheter having an inside diameter of 1.7 to 3.0 millimeters.

10. The system of claim 1 wherein said transtracheal catheter uses a high tech biopolymer having a durometer of 70–90 Shore A.

11. A method for continuous flow augmentation of ventilation and removal of $CO_2$ from a patient in an open delivery system during spontaneous breathing of providing a transtracheal catheter inserted into the trachea of a patient the patient, said method comprising the steps of:
    providing a continuous ratio of an oxygen/air mixture having at least twenty-one percent oxygen,
    selectively controlling the flow of said oxygen/air mixture at a constant flow value in a range of eight to twenty liters per minute,
    regulating the pressure of said oxygen/air mixture from said providing means at a preselected pressure in a range of two to twenty pounds per square inch,
    maintaining constant humidity and temperature values for said oxygen/air mixture said humidity values being in a range of eighty to one hundred percent and said temperature values being in a range of thirty-five to thirty-eight degrees Celcius,
    continuously delivering said oxygen/air mixture into the trachea of said patient in said tranchrocheal catheter, allowing the removal of $CO_2$ at a desired level, while allowing the respiratory muscles of the patient to relax while allowing the patient to spontaneously breathe at any time.

* * * * *